United States Patent [19]

Cammilli et al.

[11] Patent Number: 5,220,917
[45] Date of Patent: Jun. 22, 1993

[54] IMPLANTABLE PHARMACOLOGICAL DEFIBRILLATOR WITH AUTOMATIC RECOGNITION OF VENTRICULAR FIBRILLATION

[75] Inventors: Leonardo Cammilli, Via G. Caselli 11; Gino Grassi; Luciano Alcidi, all of Florence, Italy

[73] Assignee: Leonardo Cammilli, Florence, Italy

[21] Appl. No.: 614,291

[22] Filed: Nov. 16, 1990

[30] Foreign Application Priority Data

Nov. 24, 1989 [IT] Italy .................. 9568 A/89

[51] Int. Cl.⁵ .......................................... A61N 1/39
[52] U.S. Cl. ............................................ 128/419 D
[58] Field of Search ................ 128/419 D; 604/891.1

[56] References Cited

U.S. PATENT DOCUMENTS

| | | | |
|---|---|---|---|
| 3,923,060 | 12/1975 | Ellinwood, Jr. | 604/891.1 |
| 4,003,379 | 1/1977 | Ellinwood, Jr. | 604/891.1 |
| 4,291,699 | 9/1981 | Geddes et al. | 128/419 D |
| 4,552,561 | 11/1985 | Eckenhoff et al. | 604/891.1 |
| 4,774,951 | 10/1988 | Osypka | 128/419 P |
| 4,892,100 | 1/1990 | Schaldach | 128/419 PG |
| 4,969,873 | 11/1990 | Steinbach et al. | 604/891.1 |
| 5,041,107 | 8/1991 | Heil, Jr. | 604/891.1 |

OTHER PUBLICATIONS

European Search Report, The HAGUE, Jul. 5, 1991, Examiner Schmierer U. J.

Primary Examiner—William E. Kamm
Assistant Examiner—Scott M. Getzow
Attorney, Agent, or Firm—Hedman, Gibson & Costigan

[57] ABSTRACT

The invention provides an automatic implantable defibrillator with the following essential characteristics: a) reliable recognition of a ventricular fibrillation state by noting mechanical ventricular systole noise and taking action if absent; b) effecting defibrillation not by electrical pulses fed to the heart but by a bolus of medicaments (or solutions under particular physical conditions, such as a cold bolus at 30° C.) fed by a hydraulic system into the coronary sinus by a retrograde path to obtain an artificial circulation so as to rapidly pervade the coronary circuit. The symbol A.I.Ph.D. (Automatic Implantable Pharmacological Defibrillator) is proposed (D.A.I.F., Defibrillatore Automatico Impiantabile Farmacologico, in Italian).

16 Claims, 4 Drawing Sheets

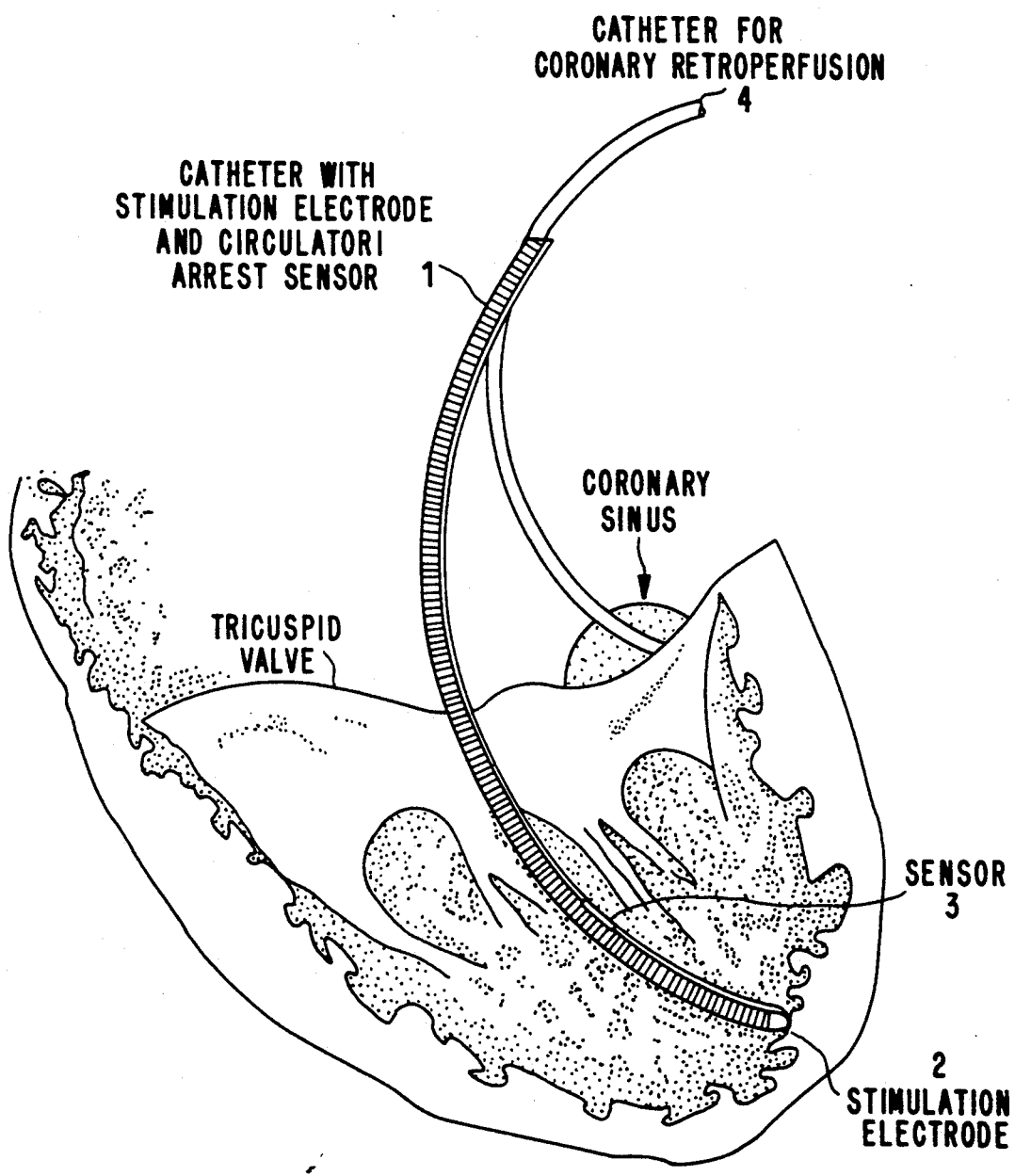

IMPLANTABLE PHARMACOLOGICAL DEFIBRILLATOR WITH AUTOMATIC RECOGNITION OF VENTRICULAR FIBRILLATION

In the known art, patients at risk from prolonged ventricular fibrillation crises are provided with automatic implantable defibrillators (symbol A.I.C.D.), generally composed of a cardiac rhythm alteration detection system able to determine ventricular fibrillation and usually designed to measure and interpret cardiac electrical signals, plus a generator which emits an electrical defibrillation pulse of the order of 20-25 J of energy. These instruments however currently suffer from numerous drawbacks which limit their use, and in addition are rather aggressive in their therapeutic action. These drawbacks include the following:

as the electrical defibrillation threshold is not constant, the action may be ineffective;
in the case of sustained ventricular tachycardia there is the risk of interpretation errors and hence of false positive indications with the probability of a worsening of the situation;
possible non-recognition of fibrillation, with consequent lack of action;
aggressive action in the case of application of epicardial patches, with a statistical mortality of 8-10%;
considerable size and weight;
possible myocardial lesion because of electric shock;
early battery wear;
considerable delay of action;
reduced ventricular filling because of patches fixed to the ventricular wall.

Thus, beside the technological availability, the A.I.C.D. is also very difficult to use.

Most of these drawbacks are obviated by the type of instrument described hereinafter.

Considering that the problems derive essentially from the difficulty of recognizing ventricular fibrillation and the impossibility of reliably defining the electrical defibrillator threshold, a system is proposed which differs in terms of these essential characteristics from those already available.

As an alternative to electrical signal analysis, ventricular fibrillation can be recognized by determination of circulatory and pump arrest based on the absence of the mechanical sound produced by ventricular contractions. If circulatory arrest is determined there are two possible causes, namely asystole or ventricular fibrillation.

The proposed apparatus then immediately produces ventricular stimulation by means of an incorporated pacemaker. If the cause is asystole the stimulation causes ventricular contraction, so restoring the alert state; the V V I stimulation proceeds if necessary, or stops if automatic rhythm is restored. If on the other hand the cause is ventricular fibrillation, the stimulation has no effect and after a few stimulations (2-4 or thereabouts) the instrument produces its defibrillation action.

This is the second novelty of the proposed system. Instead of an electric shock a system of bolus-perfusion of antiarrhythmic and antifibrillation medicaments or cooled solutions is proposed. These are fed under a certain pressure directly into the coronary circulation via a catheter in a retrograde direction, inserted chronically into the coronary sinus or into a coronary artery.

BRIEF DESCRIPTION OF DRAWINGS

FIG. 4 is a cutaway diagram of a heart with a stimulating electrocatheter and an infusion catheter in place.

On this basis the system, which is described in detail hereinafter, consists of:

A) A subcutaneous generator implant contained in a casing of biocompatible metal (such as titanium) and comprising: the electrical power unit; the reservoir which can be refilled from the outside by a hypodermic needle; the propulsive system for the bolus infusion; the V V I or dual demand pacemaker; a telemetric programming system for choosing the pacemaker parameters (duration and amplitude of the stimulus, frequency, sensing etc.) and the bolus parameters (duration and possibly quantity).

B) A venous-introduced catheter comprising: the stimulation electrode or electrodes; the noise detection sensor of piezoelectric or any other type.

C) A venous-introduced catheter with an internal lumen, to be connected to the bolus emission system.

As can be seen, in contrast to an AICD a thoracotomy is not required, but merely a simple implant similar to that for a normal pacemaker.

Figure 1:
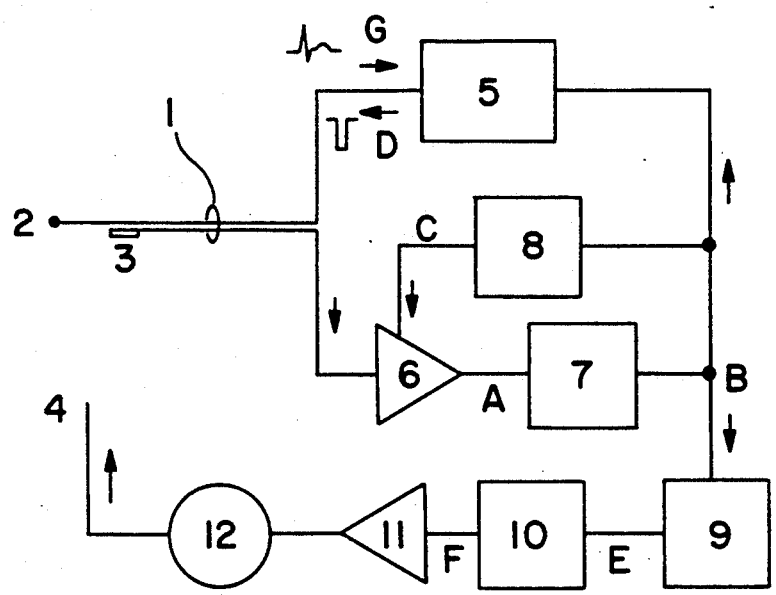
FIG. 1 is a block circuit diagram of the apparatus of the invention.
Figure 1B:
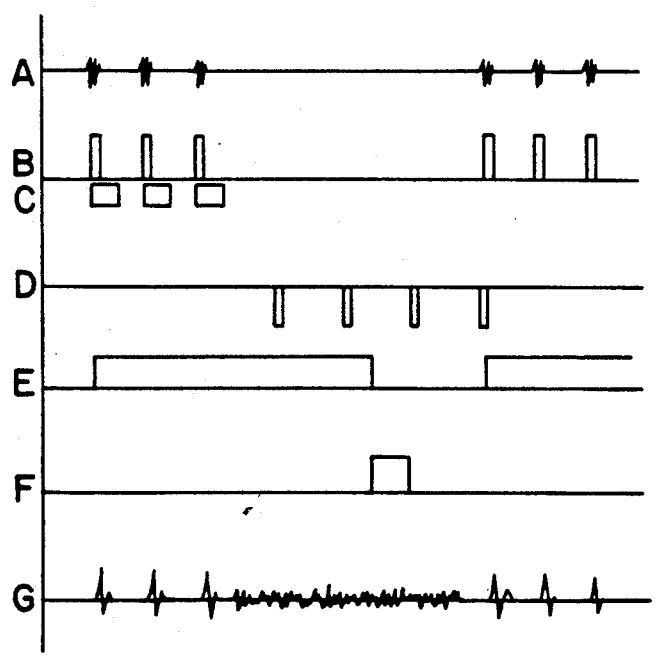
FIG. 1B is a diagram of the trigger pulses which are generated by the sensor.

With reference to FIG. 1, an example of a block circuit for obtaining the operating algorithm will now be described. An initial normal rhythm monitoring situation will be assumed. The catheter 1 is inserted venously into the patient in the manner of a normal pacemaker electrocatheter. The catheter 1 carries within its body the stimulation electrode 2 and the sensor 3 for sensing cardiac noise. This noise is caused by the movement of the cardiac muscle or by the blood flow during systolic pumping and corresponds to the initial phonocardiographic tone. Noise preceding the diastole is not sensed because of the refractory period described hereinafter. The electrical signal originating from the sensor 3 is amplified by 6 (A in FIG. 1B) to obtain an amplitude sufficient to control the circuit 7 (for example a monostable circuit) which generates a trigger pulse of constant characteristics (B in FIG. 1B). Via a monostable circuit 8, this signal triggers a signal of programmable duration so as to blank the amplifier 6 in order to inhibit it for the time required for it not to sense signals due to diastolic cardiac noise.

The signal B from 7 is also fed to the pacemaker 5 which uses it to inhibit its V V I operating generator, in parallel with the signal G sensed by the electrode catheter 2. The signal B from 7 also synchronizes a retriggerable monostable multivibrator 9, which is programmed for a signal of sufficient length to exceed the sum of 2 or 3 periods of the generator contained in the pacemaker 5. As 9 is retriggerable, the signals B from 7 maintain its output Q at level 1, so impeding operation of the timer circuit 10 which is designed to start with a negative signal. The components 11 and 12 therefore remain at rest.

The facility for telemetric programming can be provided in blocks 5, 6, 8 and 10, to allow adjustment of the stimulation and defibrillation parameters after the implant. For example, it can be programmed the frequency and amplitude of the stimulus of the pacemaker 5, the sensing amplification 6, the refractory period 8 and the duration of the pharmacological bolus by 10; if the pacemaker is of dual demand type, the upper intervention frequency in the case of tachycardia will also be programmable.

In programming the time of 10, an external program can be connected to make the time independent of the automatic circuit, so allowing continual perfusion from the outside or from the internal reservoir.

It will now be assumed that a ventricular fibrillation episode begins. The cardiac noise becomes a murmur which is not sensed by the system comprising the sensor 3 and amplifier 4, so that the monostable circuit 7 is no longer synchronized and no longer emits the signals B. After the set time the pacemaker 5, which is no longer inhibited by the signal B or by the signal G received from the electrode 2, commences stimulation via 2.

As the cardiac muscle is in fibrillation the stimulus cannot be effective. Thus after the time programmed for 9, this multivibrator changes state from 1 to 0 to trigger the timer 10. This operates the propulsive system 12 for infusion of the bolus of antifibrillation medicaments, this system being controlled by the actuator 11. An embodiment of this system is described hereinafter. The medicament bolus is injected into the coronary circuit by the tubular catheter 4, which is inserted into the coronary sinus or otherwise into a coronary artery. The duration of the signal F is adjusted on the basis of the quantity of medicament required to arrest fibrillation.

When this happens, the stimuli emitted by the pacemaker 5 stimulate the heart if this is not able to restart spontaneously. In either case (stimulated heart or spontaneous rhythm) the normal monitoring conditions are restored, with the return of the cardiac noise signals B and the relative electrical signal G.

If however the circulatory arrest is due to an AV block or an asystole, the pacemaker continues to stimulate until a spontaneous rhythm at higher frequency is restored. In this case the electrical pacing pulses continue in D and therefore E remains at high level, thus not allowing the bolus emission controlled by E, which is always at level 0.

An embodiment of the infusion system for the pharmacological bolus will now be described.

This system can be in the form of any mechanical and/or electrical system able to rapidly feed a sufficient quantity of medicament into the vein. It can consist for example of a rotary electric pump (peristaltic or not), a linear electromagnetic pump or an elastic mechanical system. By way of example, a hydropneumatic system has been chosen, which can result in a reduction in the size and weight of the implant as it requires little electrical power and allows the battery to be used almost exclusively by the monitoring and stimulation circuit, with the mere addition of a small solenoid valve.

Figure 2:
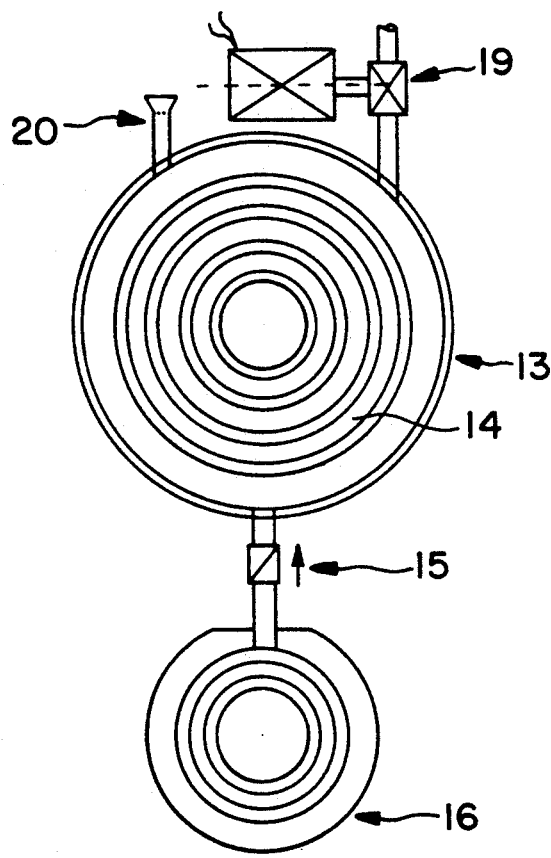
FIGS. 2, 2B are drawings of a hydropneumatic system for ejecting a quantity of medicament into a vein.
Figure 2B:
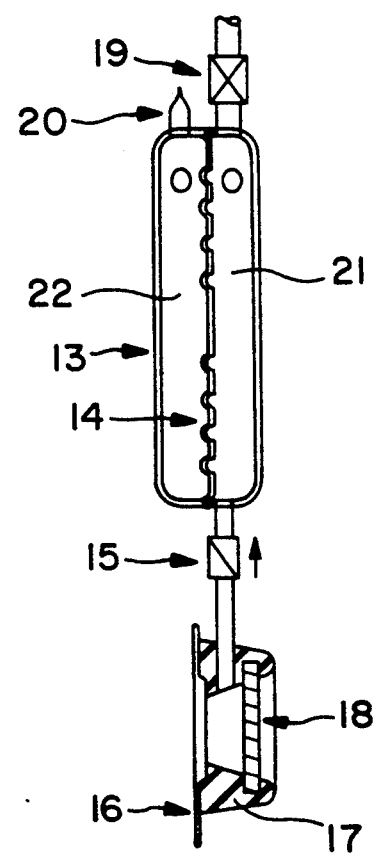

FIG. 2 shows one embodiment of such an apparatus.

The arrangement of the various components of the bolus emission part shown in the figure can be actually used in practice, however the components can also be grouped and arranged in such a manner as to reduce the implant dimensions. In the figure the access port 16 for the necessary filling of the medicament reservoir 21 is shown separated from the reservoir structure. This arrangement can be used in practice as it makes the point for injection filling more easily recognizable from the outside.

Alternatively, the port 21 could be located on the structure of the system 13 in a position corresponding with the reservoir 21, in such a manner as to project from the structure of the implanted system and be easily locatable under the cutis.

On this basis it can be seen that the described system comprises essentially the hydropneumatic system 13, the access port 16 for filling, and the solenoid valve 19 for emission of the bolus. The system 13 is composed of a capsule, which can consist, as in the figure, of two shells welded together in such a manner as to contain in their centre a flexible membrane 14 which in the figure is shown by way of example as a thin elastic plate of biocompatible metal (such as 316 stainless steel) made flexible by undulation pressing. It can however be of elastic plastics materials (latex, silicon rubber or the like).

The chamber must be of sealed assembly.

The part 22 of the system contains an inert gas compressed to a pressure sufficient to overcome the resistance of the external circuit to be fed with the pharmacological bolus.

This gas is fed in through a tube 20 which is rigid with the chamber 22 and is hermetically sealed after filling. The chamber 21 is filled with the medicament to the extent of overcoming the pressure of the gas present in 22 by displacing the flexible membrane towards the outer wall of 22.

The following are connected to the chamber 21 either directly or via tubes: the access port 16 with a series-connected unidirectional non-return valve to prevent liquid flowing back to the port, and the solenoid valve 19 (controlled by the circuit 11 of FIG. 1) which by its opening time determines the quantity of bolus injected.

The door 16 is constructed on the standard basis, in the manner for example of access port for the injection of anesthetic liquids for analgesia, namely a resin piece bonded to a metal disc and a self-sealing rubber closure membrane to form a small prechamber 17 connected to the chamber 21 via the tube and non-return valve 15. Filling is by a percutaneous needle through the rubber 18.

The system constructed in this manner is simple and does not require electrical energy, and in addition is in practice rechargeable from the outside. The filling procedure also resets the position of the membrane 14 such that the gas pressure is still active. Filling is by a system comprising a hypodermic needle, which perforates the port membrane 18 and is connected to a vessel containing the pharmacological liquid at a pressure slightly higher than that of the gas in the chamber 22, the system automatically halting delivery when the pressure reaches the value indicating maximum filling of 21.

The reservoir 13 can be of a different shape than the circular cross-sectional shape shown in the example for simplicity of representation. The outlet of the solenoid valve 19 must be connected to the catheter to be inserted into the coronary sinus or otherwise into the coronary circulation.

Figure 3:
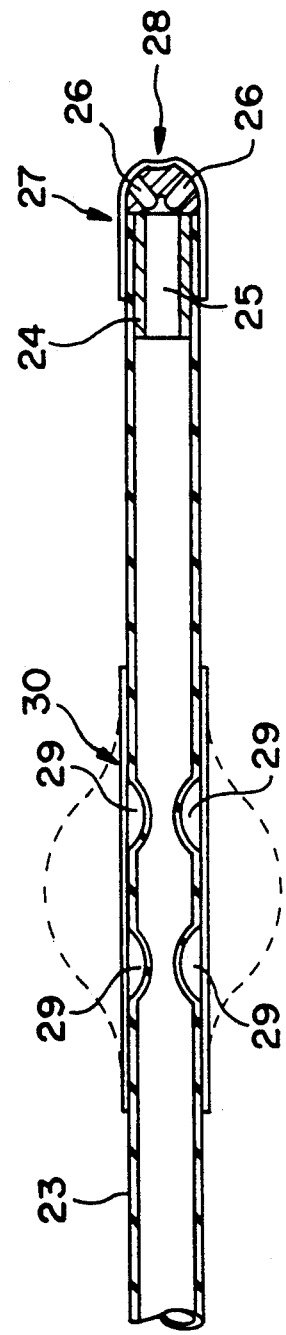
FIG. 3 is a transverse cross section of a catheter for use with the device of FIG. 2.

This catheter must have the following characteristics (see FIG. 3):

a) Small dimensions to allow easy positioning; a diameter of between 1 and 3 mm for the tube 23 can be acceptable.

b) Its distal part should possibly, but not indispensably, comprise a system which prevents blood flowing back into the catheter, to prevent the formation of thrombi which could obstruct it, in which respect in addition to this mechanical system the antiarrhythmic pharmacological medicament can be mixed with heparin or the like. A non-limiting example of a possible arrangement is shown in FIG. 3, in which the tube 23 carries an endpiece which directs the liquid to the outside through the holes 25 and 26. A thin elastic cap 27 (for example of latex or a similar material) is fitted by gluing at its proximal part onto the endpiece 24, the cap comprising in its distal part a hole which is made such that it is not normally in contact with the holes in the endpiece 24. When the pressurized liquid is emitted, its pressure moves the elastic cap forward so that the holes 26 and 28 communicate, to enable the liquid to emerge. When in its rest position blood is unable to enter.

c) Immediately upstream of the distal exit of the catheter there can be provided, optionally for the purposes of the invention, a system which blocks the vessel into which the catheter is introduced so that the bolus liquid is unable to flow backwards into the vessel but is injected only into the coronary circulation.

This could take the form of a portion of the catheter having in its wall holes 29 covered with an elastic sleeve 30 of such thickness that the pressure exerted by the injection system is sufficient to inflate this segment in the manner of a balloon.

The entire described system can be contained in a single casing on which connections are provided for the stimulating electrocatheter and sensor and for the bolus infusion catheter. This however is not essential for the purposes of the invention, which can be constructed in the form of two or more units connected together. FIG. 4 shows how the two catheters can be inserted into the heart through the venous system, as in the case of a normal pacemaker implant.

We claim:

1. An automatic self-powered implantable defibrillator with a structure containing a rechargable reservoir (13) for a medicament or a solution to be injected and a flexible catheter (4) for injecting the medicament which is connected to the outlet of said reservoir (13) and is inserted into the coronary circulation or through the coronary sinus, characterised by comprising:
   means (3) inserted into a venous-introduced catheher (1) for determining the state of the circulation;
   means (6-11) for receiving and interpreting the signal transmitted by said means (3) for determining the state of the circulation, to enable fibrillation to be detected;
   means (12) for injecting the medicament from said reservoir (13) via a flexible catheter (4) at a predetermined pressure, and activated by the fibrillation detection means (6-11) on detection of fibrillation, wherein said flexible catheter (4) is provided in proximity to its distal end with a device (29-30) for preventing backward flowing towards the cardiac cavity of the medicament injected towards the coronary cavity, in order to achieve an artificial circulation within the coronary district.

2. A defibrillator as claimed in claim 1, characterised in that said means (3) for determining the circulation state consist of a sensor for sensing cardiac noise, said means (6-11) detecting the fibrillation state, to consequently activate the medicament injection means (12) should cardiac noise be absent.

3. A defibrillator as claimed in claim 1, characterised in that said means (3) for determining circulation state consist of one or more flow and/or pressure transducers and/or transducers of other parameters which indicate the presence of ventricular fibrillation, said means (6-11) detecting the fibrillation state, to consequently activate the medicament injection means (12) in the case of absence of minimization of said parameters.

4. A defibrillator as claimed in claim 1, characterised in that said flexible medicament injection catheter (4) is provided at its end with a non-return device (24-27).

5. A defibrillator as claimed in claim 4, characterised in that said non-return device comprises an endpiece (24) with two V-arranged holes (25, 26) inserted into the distal end of the catheter (23) and a thin elastic cap (27) with its proximal part fixed onto said endpiece (24) and its distal part provided with a central exit hole (28) which communicates with the holes (25, 26) of the endpiece (24) when the cap (27) is subjected to the pressure of the medicament during injection and is intercepted in the absence of pressure.

6. A defibrillator as claimed in claim 1, characterised in that said device for preventing backward flowing towards the cardiac cavity of the medicament comprises a thin elastic sleeve (30) disposed about a plurality of holes in the catheter (4) to deform in the manner of a balloon under the pressure of the medicament during its injection.

7. A defibrillator as claimed in claim 1, characterised in that said means for injecting the medicament at a predetermined pressure comprise a flexible membrane (14) which divides the reservoir (13) into a first chamber (21) for the medicament and a second chamber (22) for a biologically inert gas under a predetermined pressure, and a solenoid valve (19) which is connected between said first chamber (21) of the reservoir (13) and the flexible injection catheter (4).

8. A defibrillator as claimed in claim 7, characterised in that said first chamber (21) of the reservoir (13) is connected via a unidirectional non-return valve (15) to an access port (16) provided with a rubber diaphragm (18) to be perforated by a percutaneous needle to enable said chamber (21) to be filled with said medicament from the outside at a predetermined pressure.

9. A defibrillator as claimed in claim 8, characterised in that said access port (16) is separated from the reservoir (13) to enable its location to be optimized.

10. A defibrillator as claimed in claim 1, characterised in that said medicament injection means 12 consist of an electric pump.

11. A defibrillator as claimed in claim 1, characterised in that said means (6-11) for receiving and interpreting the signal transmitted by the means (3) for determining the circulation state, and for activating the injection means (12), comprise an input amplifier (6) for the signal from the means for determining the circulation state, a retriggerable monostable multivibrator circuit (9) which receives trigger pulses from said monostable circuit (7), a timer circuit (10) controlled by said multivibrator (9) for determining the medicament injection time, and an output amplifier (11) for the timed operating signal.

12. A defibrillator as claimed in claim 11, characterised in that while fibrillation is not detected the output amplifier (11) and the medicament injection means (12) are at rest.

13. A defibrillator as claimed in claim 10 or 11, characterised in that said means for receiving and interpreting the signal transmitted by the means (3) for determining the circulation state comprise a monostable circuit (8) connected in parallel with said monostable synchronization circuit (7) for the multivibrator (9), to generate a signal for inhibiting the input amplifier (6) for a time corresponding to that of the cardiac noises.

14. A defibrillator as claimed in claim 13, characterised by comprising a cardiac stimulator (5) of V V I or dual demand type provided with a sensing and stimulation electrode (2) contained within a venous-inserted catheter connected to the output of the monostable circuit (7) to allow inhibition of its V V I operating generator by the synchronization from the said monostable circuit (7), said multivibrator circuit (9) being programmed for a signal of duration exceeding 2 or 3 periods of the cardiac stimulator generator, so that its output inhibits said timer (10).

15. A defibrillator as claimed in claim 14, characterised in that said determining sensor (3) and the cardiac stimulation electrodes (2) are inserted into the same venous-introduced catheter (1).

16. A defibrillator as claimed in claim 14 or 15, characterised by comprising a system for telemetrically programming the parameters of the means (6–11) for receiving and interpreting the signal transmitted by the circulation state determination means (3) for the purpose of detecting fibrillation and for activating the medicament injection means (12), namely the amplification of the received signal, the duration of the signal for inhibiting the input amplifier, and the time of operation of the medicament injection means (12).

* * * * *